United States Patent [19]
Olson et al.

[11] Patent Number: 5,897,576
[45] Date of Patent: Apr. 27, 1999

[54] AUTOMATED EXTERNAL DEFIBRILLATOR WITH THE ABILITY TO SENSE TEMPERATURE

[75] Inventors: Kenneth F. Olson, Edina; Gary B. Stendahl, Crystal; Michael A. Tvedt, Savage; Michael D. Welsch, Woodbury, all of Minn.

[73] Assignee: SurVivaLink Corporation, Minneapolis, Minn.

[21] Appl. No.: 09/057,412

[22] Filed: Apr. 8, 1998

Related U.S. Application Data

[60] Provisional application No. 06/041,813, Apr. 8, 1997.

[51] Int. Cl.$^6$ .................................................. A61N 1/39
[52] U.S. Cl. ................................. 607/5; 607/7; 607/29
[58] Field of Search ................................ 607/5, 6, 7, 63, 607/33, 34, 27, 29

[56] References Cited

U.S. PATENT DOCUMENTS

| | | | |
|---|---|---|---|
| 3,746,005 | 7/1973 | Thaler et al. ........................ | 607/29 |
| 4,080,558 | 3/1978 | Sullivan ............................... | 607/5 |
| 4,140,131 | 2/1979 | Dutcher et al. ...................... | 607/29 |
| 4,590,943 | 5/1986 | Paull et al. . | |
| 5,162,741 | 11/1992 | Bates . | |
| 5,224,870 | 7/1993 | Weaver et al. ...................... | 607/5 |
| 5,483,165 | 1/1996 | Cameron et al. . | |
| 5,741,305 | 4/1998 | Vincent et al. ..................... | 607/5 |

*Primary Examiner*—William E. Kamm
*Assistant Examiner*—Kennedy J. Schaetzle
*Attorney, Agent, or Firm*—Patterson & Keough, P.A.

[57] ABSTRACT

The AED of the present invention has a housing and a removable power supply, contained within its own power supply case, that is connected to a circuit for generating a defibrillation pulse. The circuit is electrically connectale to a pair of electrodes for delivering the defibrillation pulse. the AED further includes a temperature sensing device that is mounted inside the power supply case and connected to the power supply. The temperature sensing device senses the temperature in the power supply case and enables the adjustment of the operating parameters of the AED according to the sensed temperature.

16 Claims, 4 Drawing Sheets

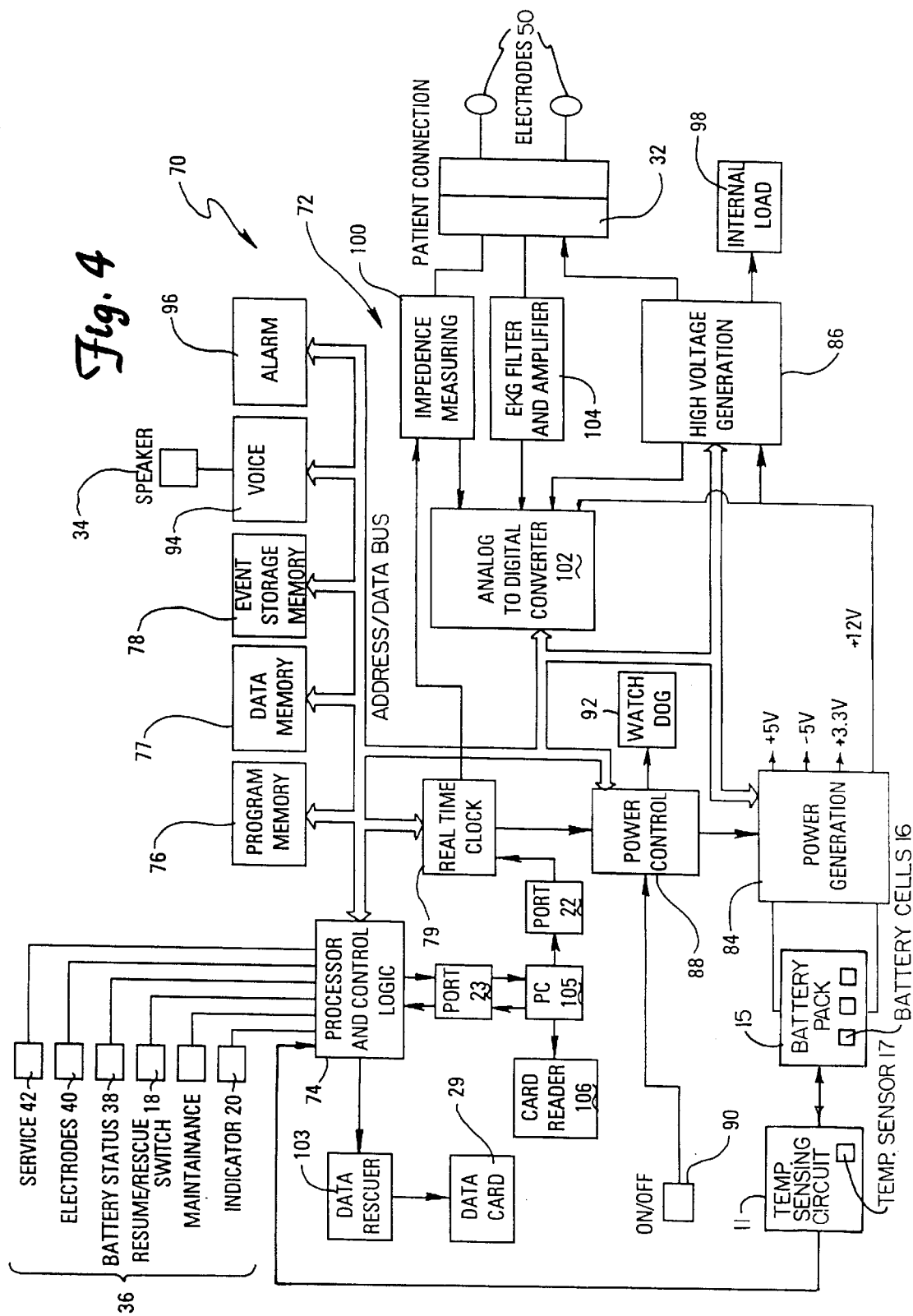

5,897,576

AUTOMATED EXTERNAL DEFIBRILLATOR WITH THE ABILITY TO SENSE TEMPERATURE

RELATED APPLICATION

This application claims the benefit of U.S. Provisional Application No. 60/041,813, Filed Apr. 8,1997.

TECHNICAL FIELD

The present invention relates generally to automated external defibrillators. In particular, the present invention is an automated external defibrillator having a temperature sensing circuit adapted to sense the temperature of the battery powering the automated external defibrillator and to adjust the expected operation of the automated external defibrillator according to the sensed temperature.

BACKGROUND OF THE INVENTION

Cardiac arrest, exposure to high voltage power lines and other trauma to the body can result in heart fibrillation which is the rapid and uncoordinated contraction of the cardiac muscle. The use of external defibrillators to restore the heartbeat to its normal pace through the application of an electrical shock is a well recognized and important tool for resuscitating patients. External defibrillation is typically used in emergency settings in which the patient is either unconscious or otherwise unable to communicate.

Automated external defibrillators or AEDs are used by police officers, paramedics and other first-responder emergency medical technicians to resuscitate cardiac arrest patients. It is important that the AEDs carried by these technicians be quickly operational after powering up and that they not provide false alarms that might delay rescue. It is essential that in a high stress situation of cardiac arrest, the technician be able to rely on the operability of the AED. Studies have shown that the chances of successfully resuscitating the patient decreases approximately ten percent per minute following cardiac arrest.

AEDs are portable devices that may find themselves in various locations such as the trunk of a car or storage bin of an emergency vehicle. Because of their portability and the variable locations, AEDs are often subject to extreme temperature variations. The batteries contained within and adapted to power the AED are also subject to these extreme variations. A battery subject to extreme cold will typically take longer to charge the AED than a battery at room temperature and thus, may indicate to the user of an AED a false indication of a low battery. Further, AED electrodes subject to very cold temperatures are likely to freeze and in doing so, provide a false indication that the electrodes are inoperable when in fact, they need only quickly thaw to be operable. There is, therefore, a need for an automated external defibrillator with the ability to sense the temperature of the battery powering the AED and to adjust the operating parameters of the AED according to the sensed temperatures.

SUMMARY OF THE INVENTION

The problems outlined above are in large measure solved by an automated external defibrillator (AED) with the ability to sense temperature in accordance with the present invention. The AED of the present invention has a housing and a removable power supply, contained within its own power supply case, that is connected to a circuit for generating a defibrillation pulse. The circuit is electrically connectable to a pair of electrodes for delivering the defibrillation pulse. The AED further includes a temperature sensing device that is mounted inside the power supply case and connected to the power supply. The temperature sensing device senses the temperature in the power supply case and enables the adjustment of the operating parameters of the AED according to the sensed temperature.

DESCRIPTION OF THE DRAWINGS

FIG. 4 is a block diagram of an electrical system of the AED shown in FIGS. 1 and 3.

DETAILED DESCRIPTION

Figure 1:
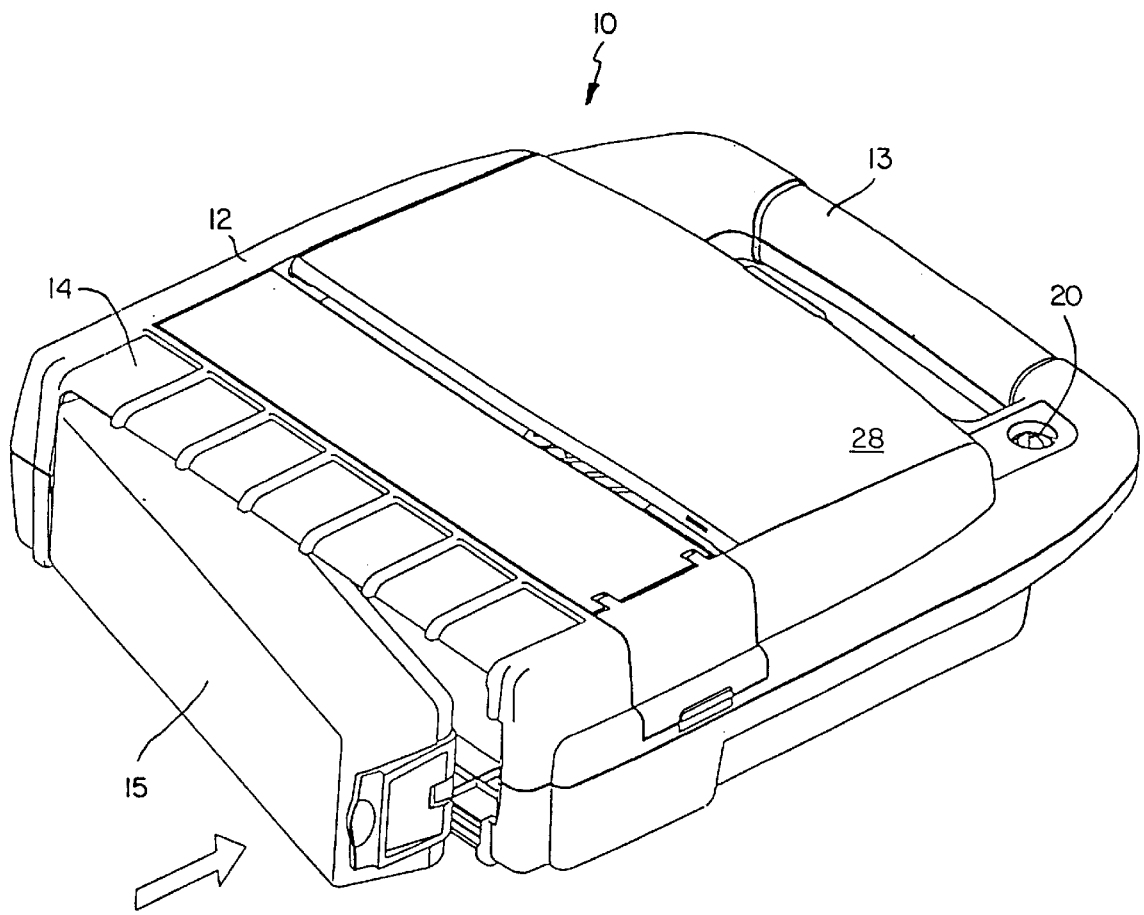
FIG. 1 is a rear perspective view of an automated external defibrillator (AED) of the present invention with a battery pack mounted thereto.
Figure 2:
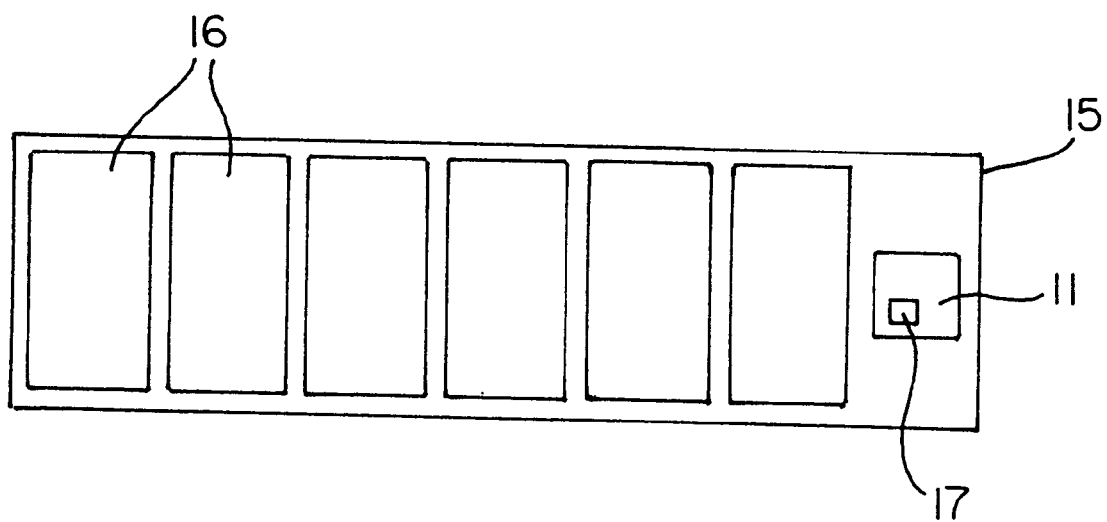
FIG. 2 is a cut away view of the battery pack including a temperature sensing circuit.
Figure 3:
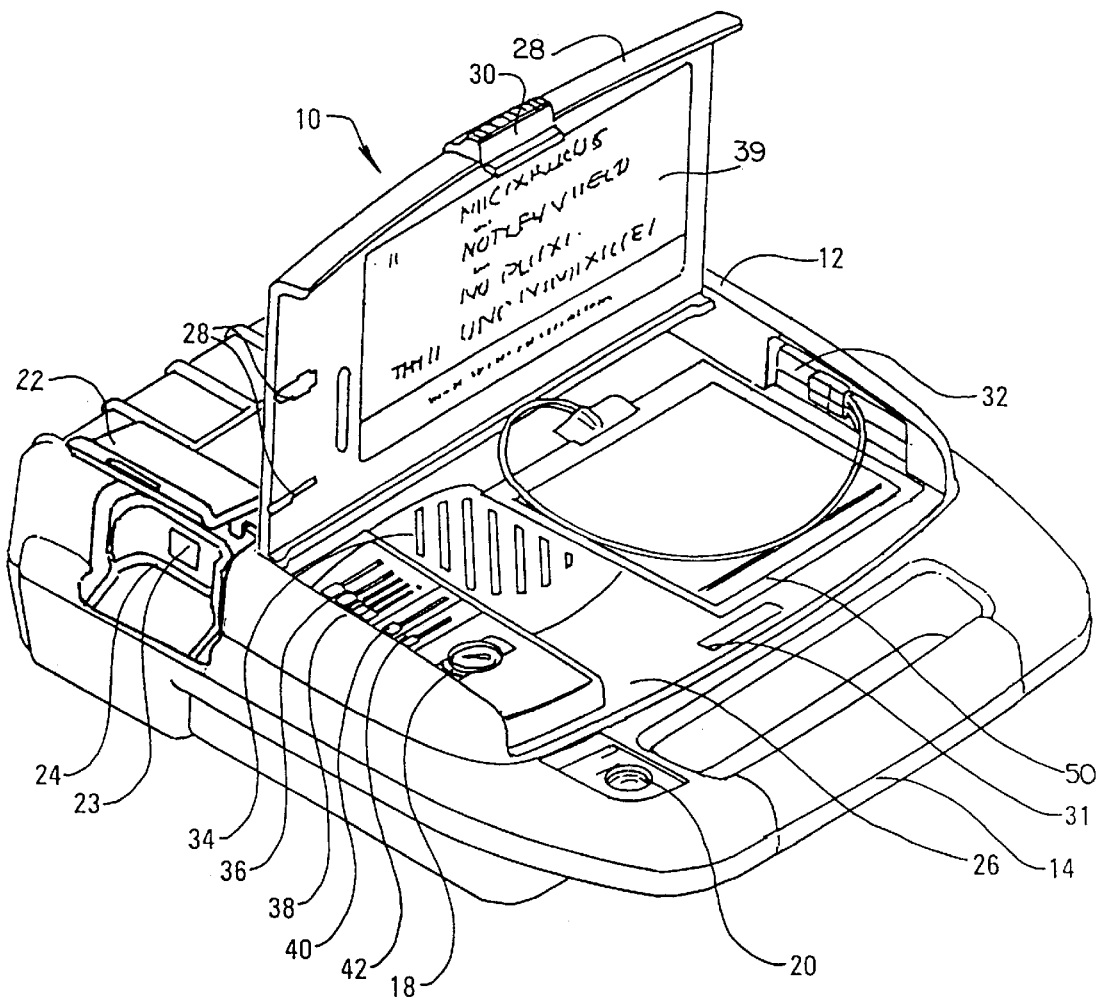
FIG. 3 is a front perspective view of the AED.

Referring to FIGS. 1–4, an automated external defibrillator (AED) 10 having a temperature sensing circuit 11 in accordance with the present invention may be appreciated. As shown, AED 10 includes a plastic housing or case 12 with a carrying handle 13 on the top portion. A removably attached battery case or battery pack 15 which contains a plurality of battery cells 16 snaps into the case 12. Temperature sensing circuit 11 is mounted in battery pack 15 proximate battery cells 16 and incorporates a temperature sensor 17. In the preferred embodiment of the present invention, circuit 11 is a Dallas semiconductor chip having part number DS2434, however, other integrated circuits having a temperature sensor portion could also be used without departing from the spirit or scope of the invention.

A visual maintenance indicator 20 and a data access door 22, which conceals a serial connector port 23 and a data card slot 24, are located on the outside of case 12 for easy access by an operator. Case 12 also includes an electrode compartment 26 defined in the top portion of case 12. A resume/rescue switch 18 (depicted in FIG. 3) is disposed adjacent to electrode compartment 26. Electrode compartment 26 is enclosed by lid 28 which is mounted to case 12 by hinges (not visible). Lid 28 covers resume/rescue switch 18 when lid 28 is in the closed disposition, as depicted in FIGS. 1 and 4. Resume/rescue switch 18 is actually a single switch with illuminatable labels alternatively indicating the "resume" or the "rescue" function, "rescue" appearing above switch 18 and "resume" appearing below switch 18, depending on whether AED 10 is cuing the operator to perform a rescue or resume operation by activating switch 18.

A bayonet-type releasable latch 30 holds lid 28 closed when AED 10 is not in use by engaging a receiving recess 31 defined in the floor of electrode compartment 26. Lid 28 is opened by grasping the underside of latch 30, pushing in to disengage latch 30 from recess 31 and lifting upward on latch 30 to gain access to electrode compartment 26.

An electrode connector 32, speaker 34 and diagnostic display panel 36 are disposed on case 12 within electrode compartment 26. Diagnostic display panel 36 is disposed adjacent to the resume/rescue switch 18. Diagnostic display panel 36 includes visual "Battery Status" indicator light 38, "Electrodes" indicator light 40, and "Service" indicator light 42. An instruction and safety label 39 is located in the inside surface of lid 28. Electrodes 50 are removably connected to electrode connector 32. Electrodes 50 typically include a pair of electrodes for attachment to a patient in a sealed package.

FIG. 4 is a block diagram of the electrical system 70 of AED 10. The overall operation of AED 10 is controlled by a digital microprocessor-based control system 72 which includes a processor 74 interfaced to program memory 76, data memory 77, event memory 78 and real time clock 79.

The operating program executed by processor 74 is stored in program memory 76. Data memory 77 is used by processor 74 as a scratch pad memory during the execution of the operating program.

Electrical power is preferably provided by a non-rechargeable, lithium sulphur dioxide battery pack 15 that is removably positioned within the battery compartment. Battery pack 15 is preferably comprised of a plurality of battery cells 16 that are electrically connected together. Battery pack 15 is connected to power generation circuit 84. "Battery Status" indicator light 38 indicates the charge status of battery pack 15 and prompts the operator to replace battery pack 15 when needed.

During normal operation, power generation circuit 84 generates a 12 V supply and regulated 3.3 and ±5 V supplies with the power provided by battery pack 15. The 3.3 V supply is generally used to power real time clock 79, lid switch 90 and watch dog timer 92 when lid 28 is closed, or in other words, when AED 10 is in a stand-by mode. The +5 V output of power generation circuit 84 functions as a back-up battery to power components of electrical system 70 during execution of self-tests and to activate maintenance indicators and alarms (as described below). Although not separately shown in FIG. 4, power generation circuit 84 includes a voltage level sensing circuit which is coupled to processor 74. The voltage level sensing circuit provides a low battery level signal to processor 74 whenever the voltage level of battery pack 15 is less than a predetermined value. Battery pack 15 is connected to temperature sensing circuit 11 while temperature sensing circuit 11 is interfaced to processor 74.

Power generation circuit 84 is also connected to power control circuit 88 and processor 74. Power control circuit 88 is connected to lid switch 90, watch dog timer 92, real time clock 79 and processor 74. Lid switch 90 is a magnetic reed relay switch in one embodiment, and provides signals to processor 74 indicating whether lid 28 is open or closed. Serial connector port 23 is coupled to processor 74 for two-way serial data transfer using an RS-232 protocol. Resume/rescue switch 18 and the "rescue" and "resume" indications thereof, maintenance indicator 20, and "Battery Status" indicator light 38, "Electrodes" indicator light 40, and "Service" indicator light 42 of diagnostic display panel 36, voice circuit 94 and piezoelectric audible alarm 96 are also connected to processor 74. Voice circuit 94 is connected to speaker 34. In response to voice prompt control signals from processor 74, circuit 94 and speaker 34 generate audible voice prompts.

High voltage generation circuit 86 is also connected to and controlled by processor 74. High voltage generation circuits such as circuit 86 are generally known and disclosed, for example, in the commonly assigned Persson et al. U.S. Pat. No. 5,405,361, which is hereby incorporated by reference. In response to charge control signals provided by the processor 74, high voltage generation circuit 86 is operated in a charge mode during which one set of semiconductor switches (not separately shown) cause a plurality of capacitors (also not shown), to be charged in parallel to about 400 V each, by power supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 32 which is connected to high voltage generation circuit 86. Under certain circumstances described below, processor 74 causes high voltage generation circuit 86 to be discharged through an internal resistive load 98 rather than connector 32.

Impedance measuring circuit 100 is connected to electrode connector 32 and real time clock 79, and is interfaced to processor 74 through analog-to-digital (A/D) converter 102. The impedance measuring circuit 100 receives a clock signal having a predetermined magnitude from clock 79, and applies the signal to electrodes 50 through connector 32. The magnitude of the clock signal received back from electrodes 50 through connector 32 is monitored by impedance measuring circuit 100. An impedance signal representative of the impedance present across electrode connector 32 is then generated by circuit 100 as a function of the ratio of the magnitudes of the applied and received clock signals (i.e., the attenuation of the applied signal). If the conductive adhesive on electrodes 50 is dried out, if electrodes 50 are not properly connected to connector 32, or if electrodes 50 are not properly positioned on the patient, a relatively high resistance (e.g, greater than about two hundred ohms) will be present across connector 32. The resistance across connector 32 will be between about twenty-five and one hundred eighty ohms when fresh electrodes 50 are properly positioned on the patient with good electrical contacts. The impedance signal representative of the impedance measured by circuit 100 is digitized by A/D converter 102 and provided to processor 74.

AED 10 also includes a data recorder 103 that is interfaced to processor 74 and positioned internally within AED 10 adjacent to data card slot 24 so as to be ready to accept data card 29. AED 10 further includes an electrocardiogram (EKG) filter and amplifier 104 which is connected between electrode connector 32 and A/D converter 102. The EKG or cardiac rhythm of the patient is processed by filter and amplifier 104 in a conventional manner, and digitized by A/D converter 102 before being coupled to processor 74.

The rescue mode operation of AED 10 is initiated when an operator opens lid 28 to access electrodes 50. The opening of lid 28 is detected by lid switch 90, which effectively functions as an on/off switch. In response to this action, power control circuit 88 activates power generation circuit 84 and initiates the rescue mode operation of processor 74. Processor 74 then begins its rescue mode operation by switching maintenance indicator 20 to a maintenance required state (e.g., a yellow visual display in one embodiment), flashing the "rescue" light associated with resume/rescue switch 18 and the indicator lights on diagnostic display panel 36, and performing a lid opened self-test.

During the lid opened self-test, processor 74 checks at least the following: 1) the temperature of battery pack 15; 2) the charge state of battery pack 15; 3) the interconnection and operability of electrodes 50; 4) the state of event memory 78; 5) the functionality of real time clock 79; and 6) the functionality of A/D converter 102.

The temperature of battery pack 15 is checked by temperature sensing circuit 11 using temperature sensor 17. Temperature sensing circuit 11 is mounted in battery pack 15 proximate the battery cells 16 such that when battery pack 15 is inserted into AED 10, battery cells 16 and temperature sensing circuit 11 are to the interior of case 12. In this position, the temperature sensing circuit 11 is able to sense only the temperature of battery pack 15 within the interior of case 12. Sensing of the ambient air temperature to the exterior of case 12, which may be significantly different than the temperature internal to case 12, is avoided.

The interior location of temperature sensing circuit 11 is very important. For example, assume an AED 10 is stored in the trunk of a squad car during a winter night with the ambient temperature being −10° F. The following morning a patient goes into cardiac arrest and AED 10 is brought inside a home. A temperature sensor 17 positioned to the exterior of case 12 would almost instantly sense the ambient temperature of the home, which is typically between 68° and 75° F., and assume this to be the temperature of the entire AED. However, the temperature inside of battery pack 15 is of a much lower value and will take time to equalize to the ambient temperature of the home. As such, the initial response time of a chilled battery pack 15 and its battery cells 16 would not be the same as a battery pack 15 at a warmer temperature of 68° to 75° F.

In view of the above example, interiorly located temperature sensing circuit 11 is utilized to change the expected operating parameters of AED 10. In normal operation, the charge state of battery pack 15 is checked by monitoring the voltage level signal provided by power generation circuit 84. If battery pack 15 is determined to have a low charge, "battery status" indicator 38 on diagnostic display panel 36 is illuminated by processor 74. However, if temperature sensing circuit 11 has sensed that the temperature of battery pack 15 is outside a desired range (e.g. below 60° F.), processor 74 is notified that battery pack 15 has a lower voltage and will be charging more slowly than expected. As such, the expected charging characteristic is adjusted to provide additional time for charging. The fault indicating a low battery may also be adjusted to provide additional time for charging.

Further, in normal operation, the interconnection and operability of electrodes 50 are checked by monitoring the impedance signals provided by impedance measuring circuit 100. If electrodes 50 are missing or unplugged from connector 32, or if electrodes 50 are damaged, processor 74 will illuminate "Electrodes" indicator light 40 on diagnostic display panel 36. However, if temperature sensing circuit 11 detects that the temperature of battery pack 15 is out of a desired range (e.g., below 32° F.) a signal is sent to processor 74 to disable the electrode self-test portion of the AED lid open self-test routine. This is an important feature in that electrodes 50 used with AED 10 are water based. Consequently, at cold temperatures electrodes 50 freeze. When electrodes 50 freeze, the resulting measured impedance is very high. However, even though electrodes 50 are frozen, electrodes 50 are of little mass and will thaw virtually instantly into an operational state when applied to the human body. Thus, the initial detection of the high impedance across frozen electrodes 50 indicating inoperable electrodes 50 produces a false error unless the electrode test portion of the lid opened self-test routine is disabled.

Disabling the electrode self-test portion of the self-test routine at lower battery temperatures not only eliminates erroneous electrode 50 failure readings, it also saves crucial charge on nonrechargeable battery pack 15. For example, referencing the earlier scenario in which AED 10 is stored in the trunk of a squad car at −10° F., it may be presumed that electrodes 50 are frozen. Thus, when AED 10 performs its daily lid opened self-test, if the test electrode routine has not been disabled, the impedance of the electrodes will have skyrocketed thus causing an error to be detected. Visual maintenance indicator 20 will stay red indicating a fault and an audible beep will be sounded every 30 seconds. Each beep uses a small amount of current from nonrechargeable battery pack 15. Thus, each beep further depletes battery pack 15. Temperature sensing circuit 11 enables the prevention of erroneous fault indications and unnecessary depletion of battery pack 15.

Further, during the lid opened self-test, processor 74 accesses event memory 78 to determine whether data from a previous rescue operation are still stored in memory. If so, processor 74 causes the "resume" indicator associated with resume/rescue switch 18 on diagnostic panel 36 to be illuminated, and initiates the generation of a "clear memory" voice prompt. If resume/rescue switch 18 is pressed by the operator following the activation of these indicators, processor 74 clears event memory 78 and proceeds with its rescue mode operation. The functionality of real time clock 79 and A/D converter 102 are checked by monitoring the outputs of these circuit elements for expected signals. Diagnostic display panel "service" light 42 is illuminated by processor 74 if faults are identified in either of real time clock 79 or A/D converter 102.

If the lid opened self-test is successfully completed, processor 74 switches maintenance indicator 20 to an operational state and initiates the rescue mode of operation of AED 10. The rescue mode of operation generates audible voice prompts through speaker 34 to guide the user through the operations of AED 10 and if necessary, delivery of a defibrillation pulse. AED 10 determines its rescue mode steps of operation by monitoring the impedance across electrode connector 32 and by monitoring the patient's cardiac rhythm.

The closing of lid 28 after rescue mode operation activates processor 74 to initiate and perform a lid closed self-test. During the lid closed self-test processor 74 performs a comprehensive check of the status and functionality of AED 10, including: 1) the state of event memory 78; 2) the functionality of real time clock 79; 3) the functionality of A/D converter 102; 4) the functionality of program memory 76, data memory 77 and event memory 78; 5) the charge state of battery pack 15; 6) the interconnection and operability of electrodes 50; and 7) the temperature of battery pack 15. The state of event memory 78, the state of battery pack 15, the temperature of battery pack 15, the interconnection and operability of electrodes 50, and the functionality of real time clock 79 and A/D converter 102 are checked in a manner identical to that described above with reference to the lid opened self-test.

Conventional memory test routines are implemented to check the functionality of program memory 76, data memory 77 and event memory 78. Maintenance indicator 20 is switched to its maintenance required state by processor 74 if faults are identified during the lid closed self-test. No audible alarms are actuated if faults are identified in the charge state of battery pack 15 or the interconnection or functionality of electrodes 50 during the lid closed self-test.

A daily self-test is initiated and performed by processor 74 at a predetermined time each day (i.e., every twenty-four hours). During the daily self-test, processor 74 performs all the component check operations described above that are performed during the lid opened and lid closed self-tests. In addition to illuminating the appropriate lights on diagnostic display panel 36, processor 74 maintenance indicator 20 to its maintenance required state if faults are identified during the daily self-test.

Processor 74 also initiates and performs a weekly self-test at a predetermined time one day each week. During the weekly self-test processor 74 performs all the component check operations described above that are performed during the daily self-test. In addition, processor 74 causes high voltage generation circuit 86 to sequentially operate in its charge and discharge modes, with the charge being dumped to an internal resistive load 98. While high voltage generation circuit 86 is operating in the charge mode, processor 74 monitors the time required to charge the circuit's capacitors and the capacitor voltage. A fault is identified if either is out of nominal conditions. Maintenance indicator 20 and alarm 96 are actuated in the manner described above if any faults are identified during the weekly self-test. Note that all performed test and patient data may be recorded in event memory 78.

Watch dog timer 92 is set to time watch dog time-out periods of about thirty hours (i.e., a period greater than twenty-four hour periods between daily self-tests), and is reset by processor 74 at the beginning of each daily self-test and each time lid 28 is opened. In the event control system 70 malfunctions and watch dog timer 92 times out, internal hardware switches maintenance indicator 20 to the maintenance required state and processor 74 actuates alarm 96 to alert an operator to the fact that AED 10 requires maintenance.

Data representative of the operation of AED 10 and the monitored cardiac rhythm of the patient are stored in event memory 78 during rescue mode operation. Stored data representative of the operation of AED 10 includes the real time of the occurrence of each of the following events: 1) the placement of electrodes 50 on the patient, 2) the initiation of the cardiac rhythm analysis voice prompt, 3) the initiation of the charging voice prompt, 4) the completion of the charge mode operation of high voltage generation circuit 86, and 5) the actuation of rescue switch 18. The actual time base of the patient's cardiac rhythm is also stored in memory 78. Following a rescue, the stored data can be retrieved from event memory 78 through the use of a personal computer (PC) (not shown) interfaced through serial connector port 23. Real time clock 79 can also be set through the use of a PC interfaced through serial connector port 23.

Upon the completion of each lid opened, lid closed, daily and weekly self-test, processor 74 causes a record of the self-test to be stored in event memory 78. Each stored record includes data representative of the date and time of the test and the results of the test. The test results are recorded in the form of a code or other description indicating whether all the functions, components and component status states passed the test, or indicating the nature of any identified faults. In one embodiment, only the records of the ten or twenty most recently performed tests are stored in memory 78. The stored self-test records can be retrieved from memory 78 through a PC interfaced through serial connector port 23

AED 10 with temperature sensing circuit 11 offers considerable advantages. In particular, it provides temperature sensing abilities during the lid opened self-test routine of the AED that prevent erroneous error indication lights and thus, delay in the use of a perfectly operable device. Avoiding delay in the use of AED 10 works to save lives and improve the perceived reliability and dependability of the device to the operator/user.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

What is claimed:

1. An automated external defibrillator (AED) having a housing and a power supply wherein the power supply is connected to a circuit for generating a defibrillation pulse and wherein the circuit is electrically connectable to a pair of electrodes, wherein the AED has expected operating parameters, wherein the AED further includes a temperature sensing device mounted within said AED and wherein the temperature sensing device is connected to the power supply for sensing the temperature in the power supply and for enabling adjustment of the operating parameters according to the sensed temperature.

2. The AED of claim 1, wherein the temperature sensing device comprises a temperature sensing circuit incorporating a temperature sensor.

3. The AED of claim 1, wherein the power supply comprises a removable, nonrechargeable battery.

4. The AED of claim 1, wherein the operating parameters comprise a charging characteristic and wherein the charging characteristic is adjusted according to the temperature sensed by said temperature sensing device.

5. The AED of claim 1, wherein the operating parameters comprise a self-test routine and wherein the self-test routine is adjusted according to the temperature sensed by said temperature sensing device.

6. The AED of claim 5, wherein the self-test routine comprises an electrode self-test portion and wherein the electrode self-test portion of the self-test routine is enabled or disabled according to the temperature sensed by said temperature sensing device.

7. The AED of claim 1, wherein said temperature sensing device is mounted inside a power supply case.

8. An automated external defibrillator (AED) with the ability to sense temperature, the AED having a housing and a battery that is connected to a circuit for generating a defibrillation pulse and wherein the circuit is electrically connectable to a pair of electrodes, the AED having expected operating parameters, and wherein the AED further comprises:

a temperature sensing system internal to the AED, the system comprising a temperature sensing circuit electrically interfaced to the battery and to a processor, wherein the temperature sensing circuit is designed to sense the temperature of the battery and the processor is designed to enable adjustment of the operating parameters according to the sensed temperature.

9. The AED of claim 8, wherein the operating parameters comprise a charging characteristic and wherein the charging characteristic is adjusted according to the temperature sensed by said temperature sensing circuit.

10. The AED of claim 8, wherein the operating parameters comprise a self-test routine and wherein the self-test routine is adjusted according to the temperature sensed by said temperature sensing circuit.

11. The AED of claim 10, wherein the self-test routine comprises an electrode self-test portion and wherein the electrode self-test portion of the self-test routine is enabled or disabled according to the temperature sensed by said temperature sensing circuit.

12. The AED of claim 8, wherein said temperature sensing system is internal to a battery case.

13. An automated external defibrillator (AED) with the ability to sense temperature comprising:

an AED housing;

a battery proximate to the housing;

a temperature sensing circuit having a temperature sensor, said temperature sensing circuit located adjacent to said battery and temperature sensing circuit designed to sense the temperature inside of said battery; and a processor interfaced to said temperature sensing circuit, said processor designed to enable adjustment of operating parameters of the AED according to the sensed temperature.

14. The AED of claim 12, wherein the operating parameters comprise a charging characterstic and wherein the charging characteristic is adjusted according to the temperature sensed by said temperature sensing circuit.

15. The AED of claim 12, wherein the operating parameters comprise a self-test routine and wherein the self-test routine is adjusted according to the temperature sensed by said temperature sensing circuit.

16. The AED of claim 15, wherein the self-test routine comprises an electrode self-test portion and wherein the electrode self-test portion of the self-test routine is enabled or disabled according to the temperature sensed by said temperature sensing circuit.

* * * * *